United States Patent [19]
Kashanchi

[11] Patent Number: 5,527,296
[45] Date of Patent: Jun. 18, 1996

[54] HYPODERMIC NEEDLE STORAGE APPARATUS

[76] Inventor: Behnam Kashanchi, 450 N. Bedford Dr., Beverly Hills, Calif. 90210

[21] Appl. No.: 459,710

[22] Filed: Jun. 2, 1995

Related U.S. Application Data

[63] Continuation-in-part of Ser. No. 217,691, Mar. 25, 1994, Pat. No. 5,439,453.

[51] Int. Cl.$^6$ ..................................................... A61M 5/32
[52] U.S. Cl. .......................................... 604/263; 604/192
[58] Field of Search ................................... 604/192, 263, 604/187, 198, 110

[56] References Cited

U.S. PATENT DOCUMENTS 5,171,303  12/1992  DeCamp ................................. 604/192

FOREIGN PATENT DOCUMENTS 9107199  5/1991  WIPO ..................................... 604/192

*Primary Examiner*—John D. Yasko
*Attorney, Agent, or Firm*—Michael A. Painter

[57] ABSTRACT

An apparatus for storing a hypodermic needle which is adapted to permit the hypodermic needle to be removed and later recapped by relative lateral movement between the apparatus and the needle. The storage apparatus comprises a housing having an inner cylindrical chamber which is closed at one end into which the hypodermic needle may be inserted. The hypodermic needle includes an enlarged hub which engages the upper, open end of the housing. The wall of the housing chamber is longitudinally severed along the housing axis from the open upper end of the housing to the closed bottom end thereof. Sheathing tabs are secured to the outer surface of the housing, the sheathing tabs being oriented in opposition to the severed slot in the housing. The outer surfaces of the housing adjacent the severed wall of the housing chamber extend upwardly and outwardly into guide flanges which are in opposition to the sheathing tab. When suitable force is applied to the sheathing tabs, the longitudinal edges of the cylindrical wall of the housing which define the severed slot are separated thereby permitting the hypodermic needle to be removed or easily reinserted between the guiding flanges and through the lateral opening in the wall of the housing.

6 Claims, 1 Drawing Sheet

HYPODERMIC NEEDLE STORAGE APPARATUS

This application is a continuation-in-part of Ser. No. 08/217,691 now U.S. Pat. No. 5,439,453 filed Mar. 25, 1994.

BACKGROUND OF THE INVENTION

1. Field of the Invention

The present invention generally relates to apparatus for storing and recapping hypodermic needles and, more particularly, those which will prevent inadvertent puncture wounds incurred when recapping the needle.

2. Prior Art

It is well recognized that modern medical procedures make extensive use of hypodermic needles for the purpose of giving injections, blood transfusions and for taking blood samples from a patient. One of the most frequent problems which occurs as a result of using hypodermic needles, catheters and the like is the occurrence of inadvertent puncture wounds which are suffered by the practitioner while attempting to recap the hypodermic needle after use. Such inadvertent punctures often require treatment of the injury and, most importantly, in many cases require the treatment of illnesses or diseases that may result from the puncture wounds. Where injuries or illnesses occur from inadvertent puncture wounds, the user may be faced with unacceptable financial expenditures and the loss of employee time.

The problems incident to inadvertent puncture wounds cannot be underestimated. As is now recognized, one of the most deadly diseases known to man, the HIV virus, can readily be transmitted through the use of contaminated needles. In addition, diseases such as herpes, syphilis, malaria and tuberculosis may be contracted by inadvertent puncture wounds by a hypodermic needle which has been used on a patient. To address this significant problem, the prior art discloses numerous devices which attempt to prevent the occurrence of inadvertent puncture wounds while recapping or resheathing a used hypodermic needle.

One of the devices disclosed by the prior art to reduce the problem of inadvertent puncture wounds utilizes a housing having a central hole in a finger-protecting shield that allows a hypodermic needle to be inserted therethrough while being grasped during the recapping procedure. The major problem associated with this type of design is that the point of the hypodermic needle must, by necessity, be moved longitudinally with respect to the axis of the shield. Therefore, opposed lateral movement of the hypodermic needle relative to the finger-protecting shields may still result in an inadvertent puncture wound.

Another device taught by the prior art provides for covering and uncovering the hypodermic needle by relative lateral movement between he needle housing and the hypodermic needle. An elongated housing is provided with an open, elongated slot which permits insertion of the hypodermic needle into the housing and removal of the needle therefrom by relative lateral movement between the housing and the needle. The elongated slot in the housing is covered by a removable cover which, after removal, results in the exposed opening defined by the slot. The problem inherent in this device results from the open, elongated slot. Once the covering member has been removed from the elongated slot, the hypodermic needle may be inadvertently dislodged from the housing thereby providing for a continued risk of inadvertent puncture wounds.

The present invention resolves those problems inherent in the devices taught by the prior art. The present invention provides an elongated housing which is adapted to hold a hypodermic needle in an internal chamber aligned with the axis of the housing. The cylindrical wall of the housing is severed to create an opening along its longitudinal axis. In the absence of applied force, the resilient construction of the cylindrical structure of the housing causes the boundaries of the severed wall to be maintained in contact thereby preventing inadvertent exposure of the hypodermic needle. Sheathing tabs are secured to the outer wall of the housing. The orientation of the sheathing tabs relative to the opening in the wall of the housing will permit separation of the housing walls along the severed interface when force is imposed upon the tabs. A pair of guide flanges integral with the housing wall adjacent to the opening therein extend upwardly and outwardly in opposition to the tabs to aid reinsertion of the hypodermic needle within the housing. When force is imposed upon the tabs thereby separating the housing walls along the severed interface, the hypodermic needle may be removed from the housing or reinserted within the housing by laterally moving the needle between the guide flanges and the separated edges of the housing.

SUMMARY OF THE INVENTION

The present invention provides an apparatus for storing a hypodermic needle which substantially precludes the possibility of inadvertent puncture wounds. In the present invention, an elongated cylindrical housing is adapted to store a hypodermic needle before use and provides a safe enclosure for recapping and securing the needle after use. A housing having a cylindrical chamber and an open upper end and a closed bottom end is used to secure the hypodermic needle. The housing wall is severed from the open upper end to the closed bottom end. The interface between the longitudinal surfaces of the severed housing walls is aligned with and parallel spaced relation to the longitudinal axis of the housing. In its quiescent state, the resiliency of the cylindrical housing will maintain the contact between the severed surfaces of the housing walls. Sheathing tabs are affixed to the outer surface of the housing on opposite sides of the interface between the longitudinal wall edges. When appropriate forces are imposed upon the sheathing tabs, the longitudinal wall edges will be separated along the interface thereby exposing the interior of the housing. A pair of guide flanges are integral with the outer surface of the housing and are positioned on opposite sides of the severed interface in the housing wall. The guide flanges extend upwardly and outwardly in opposition to the sheathing tabs and provide an expanded guide for aiding the reinsertion of the hypodermic needle within the housing chamber. When the elongated slot is opened, the hypodermic needle may be removed or reinserted by laterally moving the needle through the severed interface thereby avoiding any movement of the needle toward the hands of the user.

It is therefore an object of the present invention to provide an improved hypodermic needle storage apparatus.

It is another object of the present invention to provide a hypodermic needle storage apparatus which minimizes the hazards resulting from inadvertent needle punctures.

It is still another object of the present invention to provide a hypodermic needle storage apparatus which permits the hypodermic needle to be removed or recapped by relative lateral movement between a housing member and the needle.

It is still yet another object of the present invention to provide a hypodermic needle storage apparatus which is simple and inexpensive to fabricate.

The novel features which are believed to be characteristic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however, that the drawing is for the purpose of illustration and description only, and is not intended as a definition of the limits of the invention.

DESCRIPTION OF THE PRESENTLY PREFERRED EMBODIMENT

Figure 1:
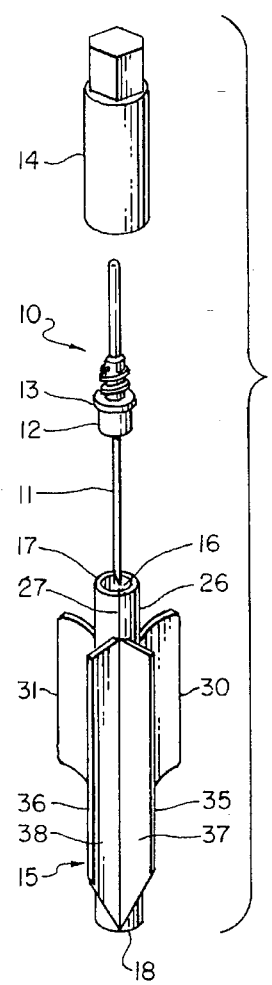
FIG. 1 is an assembly, perspective view of a hypodermic needle and a storage housing and cap in accordance with the present invention.
Figure 2:
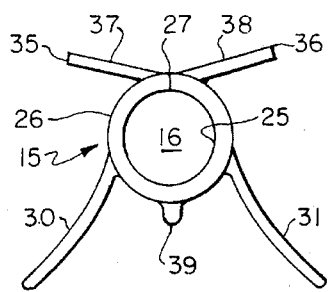
FIG. 2 is a top, plan view of the present invention hypodermic needle storage housing shown in FIG. 1.
Figure 3:
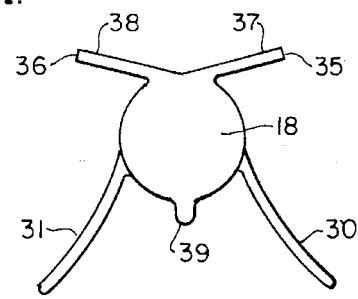
FIG. 3 is a bottom plan view of the present invention storage housing shown in FIG. 1.

The present invention hypodermic needle storage apparatus can be best understood by reference to FIG. 1 wherein an assembly view of a hypodermic needle and the storage apparatus can be best seen. In its general form, a hypodermic needle assembly 10 comprises the needle 11 and the collar 12. A seating hub 13 is typically used to align the hypodermic needle assembly 10 and is used to position the hypodermic needle assembly 10 within the present invention storage apparatus. A storage housing 15 defining an interior cylindrical chamber 26 is open at the top end 17 which is adapted to receive the hypodermic needle assembly 10 and has a closed bottom end 18. A sealing cap 14 is a cylindrical member adapted to be slidingly fit over the top end 17 of housing 15 and secure needle assembly 10 within the storage housing 15.

The structure of a preferred embodiment of storage housing 15 may be best seen in FIGS. 2, 3, 4 and 6. Storage housing 15 comprises a cylinder having annular inner and outer wall surfaces 25 and 26, respectively. Bottom end closure member 18 is integral with the walls of housing 15. As stated herein-above, it is an objective of the present invention to permit recapping a hypodermic needle assembly 10 by laterally moving the needle 11 relative to storage housing 15. To accomplish this objective, the cylindrical wall of storage housing 15 is severed from the top end 17 through to the bottom end closure member 18 creating an interface 27 between longitudinal wall edges 28 and 29 defined by inner and outer walls 25 and 26, respectively.

Interface 27 is in parallel spaced relation to the longitudinal axis of housing 15.

Housing 15 is constructed of a resilient, thermoplastic material which may be deformed when a force is applied thereto, but will return to its undeformed, quiescent condition when the force is removed. In order to allow hypodermic needle assembly 10 to be recapped in a manner contemplated by the present invention, a pair of sheathing tabs 30 and 31 are secured to outer surface 26 of housing 15 at an oblique angle relative to interface 27. Although the preferred embodiment of the present invention illustrates sheathing tabs 30 and 31 being unconnected to one another, it is understood the scope of the present invention encompasses the use of sheathing tabs 30 and 31 which are coupled at thee ends thereof.

As stated hereinabove, a primary objective of the present invention is to provide an improved storage apparatus for reinserting a used hypodermic needle 11. To enhance the margin of safety, guide flanges 35 and 36 are integral with outer surface 26 of housing 15 on either side of interface 27. Guide flanges 35 and 36 extend upwardly and outwardly from each other. The upper surfaces 37 and 38 of guide flanges 35 and 36, respectively, are adjacent longitudinal wall edges 28 and 29 and therefore provide the user with a larger surface area on which to guide the reinsertion of needle 11 into chamber 16 of storage housing 15.

Figure 4:
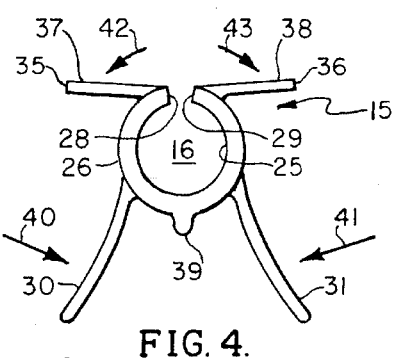
FIG. 4 is a top, plan view of the storage apparatus in its open position.

As can be seen in FIG. 4, when opposing forces 40, 41 are imposed upon sheathing tabs 30 and 31, the distance between longitudinal wall edges 28 and 29 will separate. In conjunction therewith, the distance between opposing guide flanges 37 and 38 will increase. By utilizing guide flanges 35 and 36, needle 11 may be easily reinserted within chamber 16 by guiding needle 11 along upper surfaces 37 or 38 of guide flanges 35 and 36, respectively. Since the application of forces 40, 41 on sheathing tabs 30 and 31 will increase the stress on the wall of housing 15 opposing interface 37, the wall thickness 39 between inner and outer walls 25 and 26 is increased to a distance which is greater than the remainder of the cylindrical wall.

Figure 5:
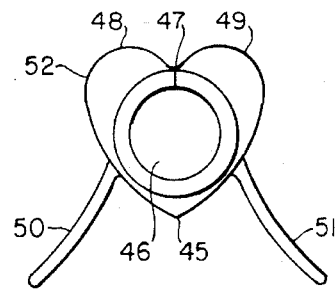
FIG. 5 is a top, plan view of an alternative embodiment of a hypodermic needle storage housing in accordance with the present invention.

An alternative embodiment for storage housing 15 may be best seen in FIG. 5 wherein the storage housing is generally referred to by reference numeral 45. In the embodiment of storage housing 45, chamber 46 is severed along interface 47 in the same manner as discussed with respect to the embodiment illustrated in FIGS. 1–4, inclusive. In place of guide flanges 35 and 36, the upper surface of housing 45 extends into surfaces 48 and 49 which depend upwardly and outwardly from interface 47. Sheathing tabs 50 and 51 are integral with the outer surface 52 of housing 45. When an inward directed forces are imposed upon sheathing tabs 50 and 51, interface 47 will separate in the same manner as described with respect to FIG. 3. When interface 47 is opened, needle 11 may be guided into chamber 46 by positioning needle 11 relative to surfaces 48 and 49.

Figure 6:
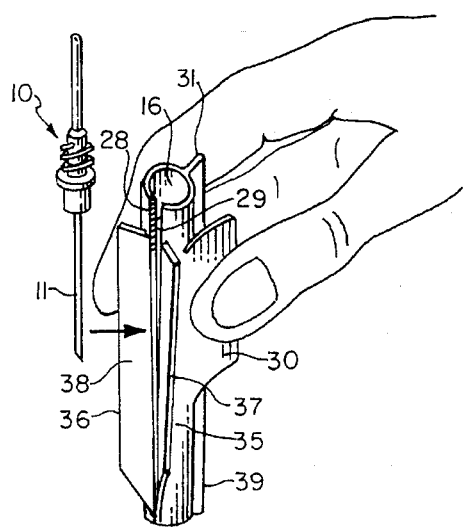
FIG. 6 is a schematic illustration showing the movement involved in reinserting a hypodermic needle within the storage housing.
Figure 7:
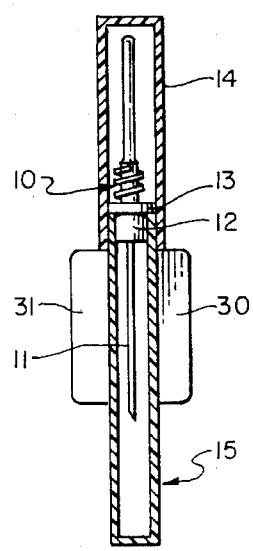
FIG. 7 is a cross-sectional view of a hypodermic needle and the present invention storage apparatus in assembled condition.

The operation of the present invention may be best understood by reference to FIG. 6 and FIG. 7. As stated, when the user applies forces 40, 41 (FIG. 4), the force components will cause storage housing 15 to be deformed with the resulting separation of longitudinal wall edges 28 and 29 in the directions designated by reference numerals 42 and 43, respectively. The deformation of storage housing 15 will be maintained so long as the inwardly directed forces 40, 41 are applied. As can be seen in FIG. 6, when longitudinal wall edges 28 and 29 are separated, hypodermic needle 11 may be inserted within housing 15 by moving the hypodermic needle assembly 10 laterally relative to storage housing 15 through the opening between longitudinal wall edges 28 and 29. Surfaces 37 and 38 of guide flanges 35 and 36, respectively, expand the target area for inserting needle 11 within chamber 16 by providing a guide to interface 27 formed by longitudinal wall edges 28 and 29. Once needle 11 is properly disposed within chamber 16 of housing 15 and forces 40, 41 removed (see FIG. 4), longitudinal wall edges 28 and 29 will again be positioned adjacent one another and needle collar 12 and seating hub 13 positioned adjacent top end 17. Needle assembly 10 may be fully recapped by slidably fitting cap 14 about outer wall 26 of storage housing 15.

It can therefore be seen the present invention provides an improved apparatus for storing and recapping hypodermic needles. When replacing a hypodermic needle after use, the needle 10 may be inserted within storage housing 15 by deforming the wall of housing 15 and separating longitudinal wall edges 28 and 29. When the longitudinal wall edges 28 and 29 are separated, needle 11 may be reinserted by relative lateral movement between needle 11 and the guide flanges 35 and 36 of housing 15. The structure of the present invention and its manner of operation avoids the necessity of moving the point of needle 11 in the direction of the hand of a user thereby precluding inadvertent puncture wounds.

I claim:

1. A hypodermic needle assembly comprising:
   (a) a hypodermic needle having a tubular collar and a needle extending axially therethrough;
   (b) a resilient needle storage housing for receiving and storing the hypodermic needle having an outer housing wall and an elongated, interior cylindrical chamber defining an open end and a closed end, said housing wall be severed from the top end to the closed end thereby defining adjacent first and second longitudinal wall edges in parallel spaced relation to the axis of said cylindrical chamber;
   (c) sheathing means for separating the first and second longitudinal wall edges secured to said housing wall on opposite sides of the first and second elongated wall edges and being obliquely oriented with respect thereto;
   (d) first and second guide surfaces integral with said housing wall and extending upwardly and outwardly from said first and second longitudinal wall edges respectively and being in opposed orientation with respect to said sheathing means; and
   (e) closure means for securing said hypodermic needle within said housing slidably coupled about the cylindrical wall of said housing adjacent the top end thereof.

2. A hypodermic needle assembly as defined in claim 1 wherein said sheathing means comprises first and second tabs, each having a top surface, said tabs being integral with said housing wall and being equally spaced from the adjacent first and second longitudinal wall edges, the top surfaces of said tabs being obliquely oriented with respect to said adjacent longitudinal wall edges whereby the first and second longitudinal wall edges will be separated upon the application of opposing forces upon the top surfaces of said tabs.

3. A hypodermic needle assembly as defined in claim 2 further including a bracing member coupled intermediate said first and second tabs.

4. A hypodermic needle storage apparatus comprising:
   (a) a resilient, elongated cylindrical housing having a wall defining an interior cavity into which a hypodermic needle is adapted to be received and stored, said wall having an open first end and a closed second end, said wall having an elongated, longitudinally disposed slot disposed between the open first end to the closed second end and extending diametrically across said closed end, said slot being defined by adjacent first and second longitudinal edges of said wall;
   (b) first and second guide flanges each integral with the wall of said housing on opposite sides of said slot and adjacent said first and second longitudinal edges respectively, said first and second guide flanges extending upwardly and outwardly from the respective longitudinal edges of said wall; and
   (c) sheathing means adapted to separate the longitudinal surfaces of said wall to permit the lateral entry of the hypodermic needle into the interior cavity of said housing secured to said wall on opposite sides of the longitudinal surfaces and being obliquely oriented with respect thereto.

5. A hypodermic needle storage apparatus as defined in claim 4 wherein said sheathing means comprises first and second tabs, each having a top surface, said tabs being secured to said wall and being equally spaced from the adjacent longitudinal surfaces, the top surfaces of said tabs being obliquely oriented with respect to said adjacent longitudinal surfaces.

6. A hypodermic needle storage apparatus as defined in claim 5 further including a bracing member coupled intermediate said first and second tabs.

* * * * *